US00PP29359P3

(12) United States Plant Patent
Sasbrink

(10) Patent No.: US PP29,359 P3
(45) Date of Patent: Jun. 5, 2018

(54) ***DAHLIA* PLANT NAMED 'BALDENINK'**

(50) Latin Name: *Dahlia variabilis*
Varietal Denomination: Baldenink

(71) Applicant: Ball Horticultural Company, West Chicago, IL (US)

(72) Inventor: Han Sasbrink, Bovenkarspel (NL)

(73) Assignee: Ball Horticultural Company, West Chicago, IL (US)

( * ) Notice: Subject to any disclaimer, the term of this patent is extended or adjusted under 35 U.S.C. 154(b) by 46 days.

(21) Appl. No.: 15/330,154

(22) Filed: Aug. 16, 2016

(65) Prior Publication Data

US 2018/0054941 P1 Feb. 22, 2018

(51) Int. Cl.
*A01H 5/02* (2018.01)

(52) U.S. Cl.
USPC ..... Plt./321
CPC ..... *A01H 5/02* (2013.01)

(58) Field of Classification Search
USPC ..... Plt./321
See application file for complete search history.

*Primary Examiner* — Keith O Robinson
(74) *Attorney, Agent, or Firm* — Audrey Charles

(57) ABSTRACT

A new and distinct cultivar of *Dahlia* plant named 'Baldenink', characterized by its semi-double type, pink-colored inflorescences having yellow tones in the center, dark green-colored foliage, and moderately vigorous, compact-upright growth habit, is disclosed.

1 Drawing Sheet

Latin name of genus and species of plant claimed: *Dahlia variabilis*.

Variety denomination: 'Baldenink'.

BACKGROUND OF THE INVENTION

The present invention relates to a new and distinct cultivar of *Dahlia* plant botanically known as *Dahlia variabilis* and hereinafter referred to by the cultivar name 'Baldenink'.

The new cultivar originated in a controlled breeding program in Venhuizen, the Netherlands during October 2009. The objective of the breeding program was the development of *Dahlia* cultivars that are freely flowering with large flowers and a moderately vigorous, compact-upright growth habit.

The new *Dahlia* cultivar is the result of open-pollination. The female (seed) parent of the new cultivar is the proprietary *Dahlia variabilis* breeding selection coded DGA08005, not patented, characterized by its double-type, white-colored inflorescences, medium green-colored foliage, and vigorous, mounded growth habit. The male (pollen) parent of the new cultivar is unknown. The new cultivar was discovered and selected as a single flowering plant within the progeny of the above stated open-pollination during August 2010 in a controlled environment in Venhuizen, the Netherlands.

Asexual reproduction of the new cultivar by terminal stem cuttings since August 2010 in Venhuizen, the Netherlands and West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Baldenink' as a new and distinct cultivar of *Dahlia* plant:

1. Semi-double type, pink-colored inflorescences having yellow tones in the center;
2. Dark green-colored foliage; and
3. Moderately vigorous, compact-upright growth habit.

Plants of the new cultivar differ from plants of the female parent primarily in flower color, flower-type, and growth vigor. The female plant has double-type, white-colored inflorescences, and a vigorous, mounded growth habit.

Of the many commercially available *Dahlia* cultivars, the most similar in comparison to the new cultivar is Dalaya Shari 'KLEDH10032', not patented. However, in comparison, plants of the new cultivar differ from plants of 'KLEDH10032' in at least the following characteristics:

1. Plants of the new cultivar have a ray floret color different from plants of 'KLEDH10032', more specifically the upper surface of fully open ray florets of 'KLEDH10032' retain a light yellow to white coloration;
2. Plants of the new cultivar have larger diameter inflorescences than plants of 'KLEDH10032'; and
3. Plants of the new cultivar have more ray florets than plants of 'KLEDH10032'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Baldenink'. The plants were grown in 4.5-inch pots for 8 weeks in a greenhouse in West Chicago, Ill.

DETAILED BOTANIC DESCRIPTION

Figure 1:
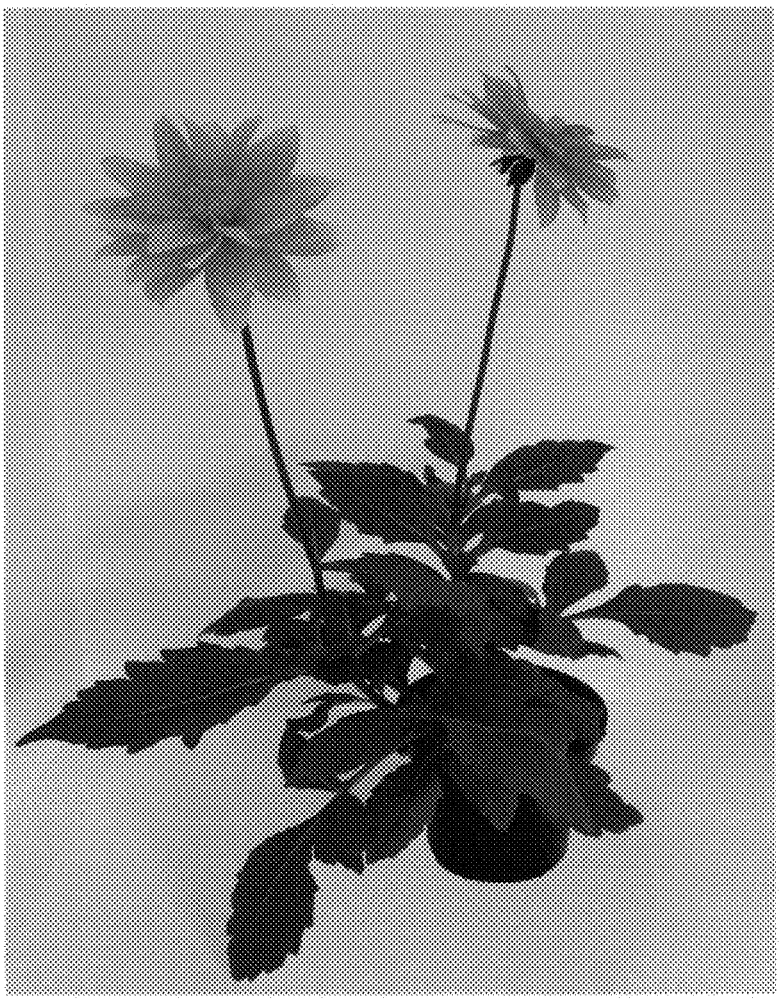
FIG. 1 illustrates a side view of the overall growth and flowering habit of 'Baldenink'.
Figure 2:
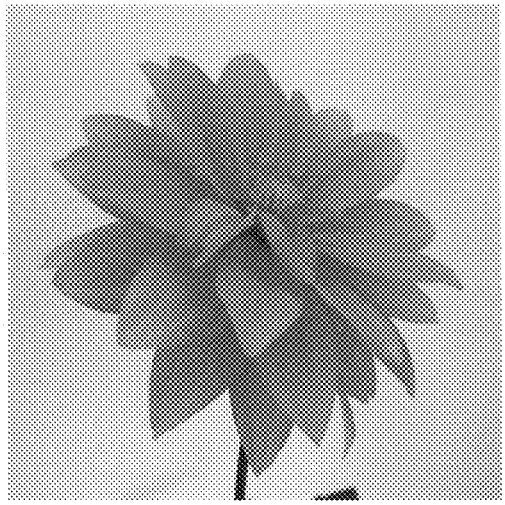
FIG. 2 illustrates a close-up view of an individual inflorescence of 'Baldenink'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2007 edition, except where general color terms of ordinary significance are used. The color values were determined in November 2015 under natural light conditions in West Chicago, Ill.

The following descriptions and measurements describe plants produced from cuttings from stock plants and grown in a glass-covered greenhouse under conditions comparable to those used in commercial practice. The plants were grown in West Chicago, Ill. in 4.5-inch pots for 8 weeks utilizing a soilless growth medium. The plants were pinched one week after transplant. Greenhouse temperatures were maintained at approximately 65° F. to 68° F. (18° C. to 20° C.) during the day and night. Greenhouse light levels of 2,500 footcandles to 6,000 footcandles were maintained during the day. Measurements and numerical values represent averages of typical plants.

Botanical classification: *Dahlia variabilis* 'Baldenink'.

Parentage:

*Female parent*.—Proprietary *Dahlia variabilis* breeding selection coded DGA08005, not patented.

*Male parent*.—Unknown.

Propagation:

*Type cutting*.—Terminal stem.

*Time to initiate roots*.—Approximately 7 to 10 days.

*Time to produce a rooted cutting*.—Approximately 28 to 32 days.

*Root description*.—Fine, fibrous.

*Rooting habit*.—Freely branching.

Plant description:

*Commercial crop time*.—Approximately 6 to 8 weeks from a rooted cutting to finish in a 15 cm pot.

*Growth habit and general appearance*.—Moderately vigorous, compact-upright.

*Size*.—Height from soil level to top of plant plane: Approximately 38.0 cm. Height from soil level to top of foliage: Approximately 15.0 cm. Width: Approximately 28.0 cm.

*Branch*.—Quantity of branches per plant: Approximately 2. Strength: Moderately strong. Length: Approximately 12.5 cm. Diameter at central internode: Approximately 6.0 mm. Texture: Glabrous. Color: 144A with an overlay of 187A. Length of central internode: Approximately 2.5 cm.

Foliage description:

*General description*.—Quantity of leaves per lateral branch: Approximately 8. Type: Simple and trifoliate. Fragrance: None. Arrangement: Opposite. Aspect: Petiole is acute angle to stem; blade is somewhat perpendicular to stem. Shape of leaf and leaflet: Elliptic. Margin of leaf and leaflet: Widely serrate. Apex of leaf and leaflet: Acute. Base of leaf and leaflet: Attenuate. Venation pattern: Pinnate.

*Simple leaf*.—Length: Approximately 10.5 cm. Width: Approximately 6.0 cm. Texture of upper and lower surfaces: Glabrous. Color of upper surface when first and fully open: Closest to N137A and venation of 147C with an overlay of 187B at base of midvein. Color of lower surface when first and fully open: Closest to 191B with venation of 147C. Length of petiole: Approximately 2.0 cm. Diameter of petiole: Approximately 4.0 mm. Texture of upper and lower surfaces of petiole: Glabrous. Color of upper and lower surfaces of petiole: 147C with an overlay of 187B.

*Mature trifoliate leaf*.—Length of mature trifoliate leaf: Approximately 12.5 cm. Width of mature trifoliate leaf: Approximately 13.5 cm. Length of terminal leaflet: Approximately 10.5 cm. Width of terminal leaflet: Approximately 5.5 cm. Length of lateral leaflet: Approximately 6.5 cm. Width of lateral leaflet: Approximately 3.2 cm. Texture of upper and lower surfaces: Glabrous. Color of upper surface when first and fully open: Closest to N137A and venation of 147C with an overlay of 187B at base of midvein. Color of lower surface when first and fully open: Closest to 191B with venation of 147C. Length of petiole of mature trifoliate leaf: Approximately 3.0 cm. Diameter of petiole of mature trifoliate leaf: Approximately 4.0 mm. Texture of upper and lower surfaces of petiole of mature trifoliate leaf: Glabrous. Color of upper and lower surfaces of petiole of mature trifoliate leaf: 147C with a faint overlay of 187B. Length of rachis: Approximately 1.0 cm. Diameter of rachis: Approximately 4.0 mm. Texture of upper and lower surfaces of rachis: Glabrous. Color of upper and lower surfaces of rachis: 147C with a faint overlay of 187B.

Flowering description:

*Flowering habit*.—'Baldenink' is freely flowering under outdoor growing conditions with substantially continuous blooming from spring through autumn and year round in the greenhouse environment.

*Lastingness of individual inflorescence on the plant*.—Approximately 2 weeks.

Inflorescence description:

*General description*.—Type: Composite, semi-double, persistent. Aspect: Facing upward and outward. Arrangement: Terminal, arising from leaf axils on strong peduncles positioned over the foliage. Disc and ray florets arranged acropetally on a capitulum. Quantity per plant: Approximately 2. Fragrance: Moderate, sweet. Shape: Rotate. Inflorescence diameter: Approximately 9.5 cm. Inflorescence depth: Approximately 4.0 cm. Disc diameter: Approximately 2.0 cm. Receptacle diameter at base: Approximately 1.1 cm. Receptacle depth: Approximately 4.0 mm. Receptacle color: 150C to 150D.

*Peduncle*.—Strength: Strong. Aspect: Erect. Length: Approximately 15.5 cm. Diameter: Approximately 4.0 mm. Texture: Glabrous. Color: 144A with a heavy overlay of 187A.

*Bud*.—Rate of bud opening: Generally takes 2 weeks for bud to progress from first color to fully open flower. Quantity per plant: Approximately 1.

*Bud just before opening*.—Shape: Oblate. Depth at first color: Approximately 1.3 cm. Diameter at first color: Approximately 1.6 cm. Texture: Glabrous. Color: Outer surface of the phyllaries is 154C with 144A at base, petals of 70A.

*Ray florets*.—Quantity per inflorescence: Approximately 34. Arrangement: Imbricate, in multiple whorls. Aspect: Slightly cupped. Shape: Elliptic. Margin: Entire. Apex: Broadly acute to having 3 acute tips. Base: Fused into a short tube. Appearance: Dull. Length: Approximately 4.3 cm. Width:

Approximately 1.7 cm. Texture of upper surface: Glabrous. Texture of lower surface: Sparsely pubescent, ribbed. Color of upper surface when first open: N74D with an overlay on approximately the lower two-thirds of 34A with 11C. Color of lower surface when first and fully open: 73B with stripes and apex of 73D. Color of upper surface when fully open: N74D with an overlay on approximately the lower half of 34A.

*Disc florets*.—Quantity per inflorescence: Approximately 58. Arrangement: Massed in center of inflorescence. Aspect: Erect. Shape: Tubular. Margin: Entire. Apex: 5 acute tips. Base: Fused. Length: Approximately 1.5 cm. Diameter at apex: Approximately 4.0 mm. Diameter at base: Approximately 2.0 mm. Texture: Glabrous. Color when fully open: 14B, translucent.

*Outer phyllaries*.—Quantity: 5 to 6. Aspect: Flat, pointed downward. Shape: Rhombic. Margin: Entire. Apex: Broadly acute. Base: Truncate. Length: Approximately 1.7 cm. Width: Approximately 8.0 mm. Texture of upper and lower surfaces: Glabrous. Color of upper surface: 137B. Color of tower surface: 137A.

*Inner phyllaries*.—Quantity: Approximately 1 per floret. Shape: Linear, imbricate. Margin: Entire. Apex: Broadly acute. Base: Truncate. Length of outermost: Approximately 2.2 cm. Width of outermost: Approximately 8.0 mm. Length of innermost: Approximately 1.0 cm. Width of innermost: Approximately 5.0 mm. Texture of upper and lower surfaces: Glabrous. Color of upper and lower surfaces: 154D, translucent with 143A at base of outermost.

*Reproductive organs*.—Androecium: On disc florets. Stamen quantity: 5 per floret. Stamen length: Approximately 8.0 mm. Anther shape: Linear. Anther length: Approximately 4.0 mm. Anther color: 1A. Pollen amount: Abundant. Pollen color: 21A. Gynoecium: On disc and ray florets. Pistil length: Approximately 1.5 cm. Stigma shape: 2 branched, perpendicular to style when fully expanded. Stigma length: Approximately 4.0 mm. Stigma color: 21A. Style length: Approximately 1.0 cm. Style color: 1A, translucent. Ovary length: Approximately 3.0 mm. Ovary color: 145D.

Seed and fruit production: Neither seed nor fruit production has been observed.

Disease and pest resistance: Resistance to pathogens and pests common to *Dahlia* has not been observed.

What is claimed is:

1. A new and distinct cultivar of *Dahlia* plant named 'Baldenink', substantially as herein illustrated and described.

* * * * *